United States Patent [19]

Tompsett

[11] 4,436,938
[45] Mar. 13, 1984

[54] MANUFACTURE OF AMINES

[75] Inventor: Alan J. Tompsett, Stockton-on-Tees, England

[73] Assignee: Imperial Chemical Industries PLC, London, England

[21] Appl. No.: 413,443

[22] Filed: Aug. 31, 1982

[30] Foreign Application Priority Data

Sep. 18, 1981 [GB] United Kingdom ............... 8128322

[51] Int. Cl.³ .................... C07C 85/06; C07C 85/02
[52] U.S. Cl. ................................ 564/474; 564/479
[58] Field of Search .......................... 564/474, 479

[56] References Cited

U.S. PATENT DOCUMENTS

| 2,882,243 | 4/1959 | Milton | 252/455 Z |
| 2,982,612 | 5/1961 | Barron et al. | 252/455 Z X |
| 3,119,658 | 1/1964 | Schulz | 23/102 |
| 3,384,667 | 5/1968 | Hamilton | 564/479 |
| 4,082,805 | 4/1978 | Kaeding | 564/474 |
| 4,191,709 | 3/1980 | Parker et al. | 564/479 X |
| 4,205,012 | 5/1980 | Parker et al. | 564/479 |
| 4,254,061 | 3/1981 | Weigert | 564/479 |
| 4,374,273 | 2/1983 | Heinsohn | 564/474 X |

FOREIGN PATENT DOCUMENTS 1567856  5/1980  United Kingdom ............... 564/479

Primary Examiner—Paul F. Shaver
Attorney, Agent, or Firm—Cushman, Darby & Cushman

[57] ABSTRACT

A process for the manufacture of methylamines comprises reacting a feed comprising methanol and/or dimethylether and ammonia over a binderless zeolite A catalyst, preferably a binderless zeolite 5A catalyst. Use of binderless zeolite 5A makes the process attractively selective to dimethylamine in preference to mono- and tri-methylamine. In addition, if the catalyst is essentially free of alkali metal it is not only more active than similar catalysts containing alkali metal but also considerably more selective.

9 Claims, 2 Drawing Figures

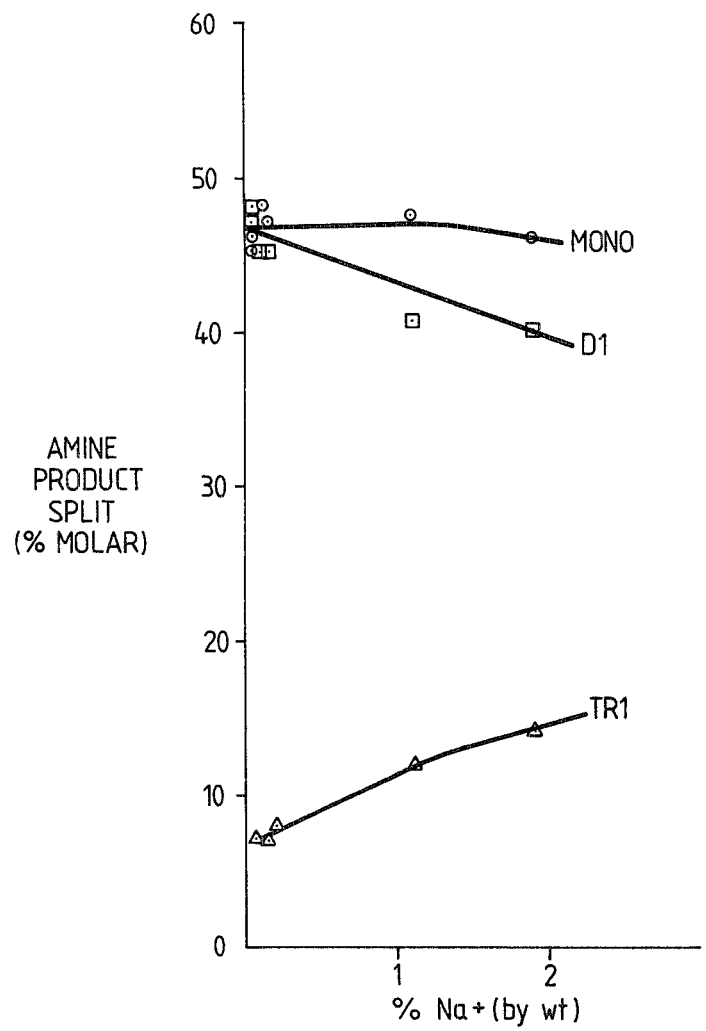

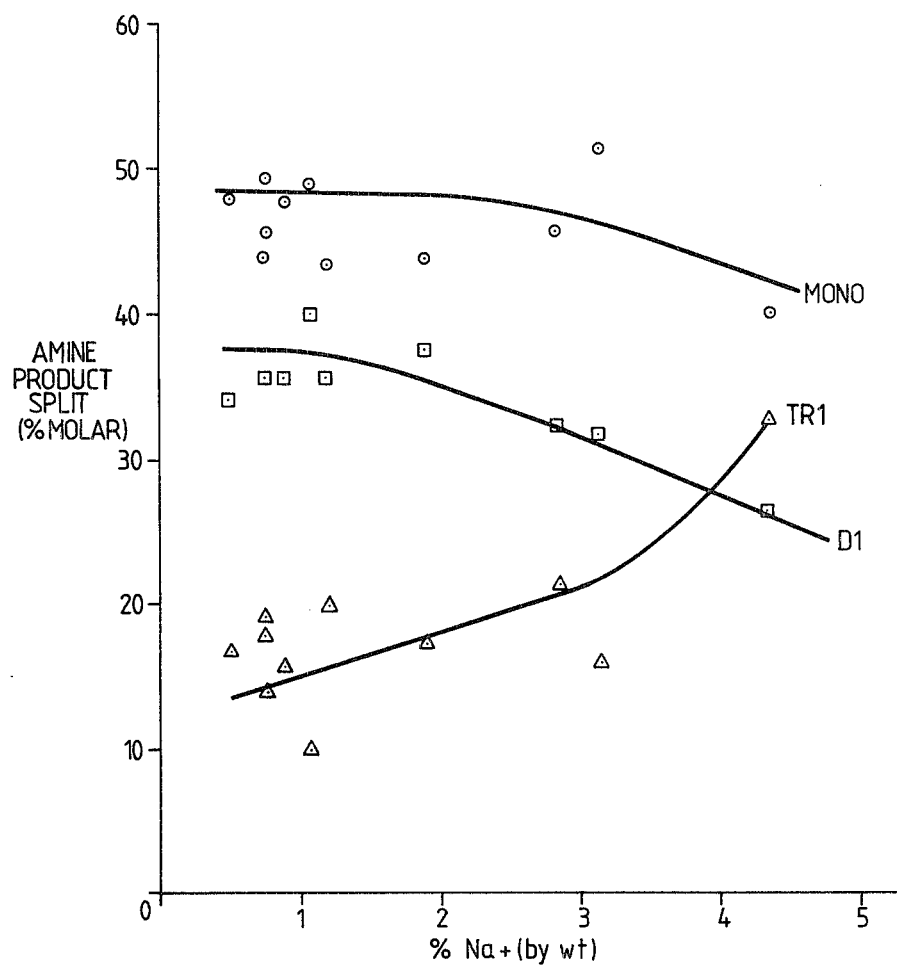

MANUFACTURE OF AMINES

The present invention relates to the manufacture of methylamines.

Lower amines, for example the three methylamines are prepared commonly by the reaction of ammonia with the corresponding alcohol, for example methanol. The reaction is usually effected in the vapour phase over a catalyst at a temperature in the range 300° to 500° C. and at a pressure in the range 10 to 30 kg/cm$^2$. The catalyst which is most frequently used, especially for the manufacture of methylamines, is a dehydration catalyst, for example an oxide such as thoria, alumina, zirconia and silica, or, most usually, a mixed silica-alumina catalyst. It has also been proposed that various crystalline aluminosilicate zeolites be used as catalysts for the manufacture of amines.

In general in the manufacture of the three methylamines, it is preferred to produce mono-methylamine (MMA) and di-methylamine (DMA) in preferance to tri-methylamine (TMA) and it is further preferred to produce di-methylamine in preference to mono-methylamine, mono- and di-methylamine being required by the market place in the greatest proportions. In methylamines manufacture, therefore, there is considerable benefit to be achieved if the catalyst is not only active but also exhibits selectivity toward the production of di-methylamine.

According to the present invention a process for the manufacture of methylamines comprises reacting a feed comprising methanol and/or dimethylether and ammonia over a catalyst comprising binderless zeolite A. Preferably, the binderless zeolite A is in the alkaline earth form, more preferably in the calcium form.

Zeolite A is a well-known synthetic crystalline zeolite whose preparation is described widely in the prior art, for example in U.S. Pat. Nos. 2,882,243 and 2,982,612. Preferably, the catalyst comprises binderless zeolite 5A, the designation "5A" indicating that the zeolite has pores whose diameter is 5 Ångstroms.

In preparing zeolite catalysts of all kinds, including zeolite A, it is usually necessary to use an inert binder or matrix material with the zeolite to achieve adequate pellet or granule strength. For example clay minerals are commonly used as binders for A type zeolites. The binder or matrix material may also act as a moderator of the high activity of the zeolite in the catalysed reaction enabling the operator to exercise greater control over the progress of the reaction.

We have now surprisingly found that the well-known process for preparing methylamines from methanol and ammonia can be made attractively selective to the production of di-methylamine by the use of a binderless zeolite A catalyst, especially a zeolite 5A catalyst. By "binderless" we mean that the catalyst contains less than 10% (as analysed by X-ray diffraction), preferably less than 5%, of a binder, matrix material or other support and it is most preferred that the catalyst contain no, or only trace amounts of, binder, matrix material or other support. However, as is well known, accurate determination of the level of impurity in zeolites is notoriously difficult and results obtained in such analysis may be subject to fairly large error. Thus, in the definition of "binderless" given above, the figure of 10% may be subject to an analytical error of as much as 50% i.e. the figure quoted should be regarded as 10±5%.

It is common practice to prepare zeolite 5A with a clay binder, usually kaolin. In the preparation of the catalyst for use in one embodiment of the process of this invention, the kaolin is removed by a high temperature technique, well-known to those skilled in this art, for example by the methods described in U.S. Pat. No. 3,119,659 and U.K. Pat. No. 1,567,856. It is unlikely that all the kaolin could ever be removed and we have found that amounts up to 10% of kaolin can be tolerated without losing all the benefits of binderless zeolite 5A in the process of this invention. Plainly, however, since the binder is non selective and may cause transmethylation of preferred methylamines at the customary reaction temperatures (so reversing the selective effect of zeolite A) it is preferred to use a catalyst with as low a level of binder as practicable consistent with adequate catalyst piece strength.

Zeolite 5A is zeolite 4A (Na form) ion-exchanged stoichiometrically with a soluble calcium salt, for example calcium chloride or calcium nitrate. In this form it is much more active for amination than it is as 4A, and it is also more selective. It is unusual for all the sodium to be removed but we have also found that for optimum results, it is better to use a catalyst which is essentially free from alkali metal. An alkali metal-free catalyst is not only more active than one containing alkali metal, it is also very considerably more selective to di-methylamine. Preferably, the catalyst has a content of alkali metal which is less than 4% by weight, more preferably less than 1% by weight and most preferably is essentially alkali metal-free, where this can be achieved without otherwise damaging the catalyst. The calcium level in zeolite 5A corresponding to these low sodium levels is normally >8% by weight, most typically 11 to 12% by weight. Zeolite A containing one or more other alkali metals, alkaline earth metals and rare earth metals, for example potassium, magnesium and lanthanum may be used as catalyst in the process of this invention but calcium would appear to be the most beneficial cation in a methanol amination zeolite A catalyst.

It is also desirable in the process of this invention to use a binderless zeolite A which has been suitably aged, that is to say zeolite A which is not freshly prepared but which has been already subjected to several days, say 1 to 5 days, use since being prepared. We have found that the behaviour of freshly prepared binderless 5A zeolite may be less than optimal. It may be hyperactive and either unselective or only partially selective. We have also found that often, after the initial ageing, further minor improvements in selectivity may take place during periods of up to 4 weeks on line. We believe that the anomalous behaviour of freshly prepared zeolite may be caused by the non-selective effect of acidic sites in the traces of binder remaining after preparation of the zeolite along with small amounts of amorphous silica-alumina. Such sites would appear to be rapidly deactivated by sintering, coke deposition or some related mechanism.

To achieve optimal results in the process of this invention in terms of yield of mono- and di-methylamine it is preferred to use lower temperatures than are usually used in methylamines processes and to operate isothermally so far as is possible consistent with adequate reactant feed rates and levels of reactant conversion that do not entail excessive recovery and recycle of unreacted methanol or dimethyl ether. Where isothermal operation is not possible, it is preferred to keep the maximum temperature as low as possible and to keep the temperature profile in the process reactor as flat as possible. Preferably the process is operated at a temperature in the range 325° C. to 400° C., this range being some 50° C. lower than the temperature range conventionally used in methylamines manufacturing processes based on amorphous silica-alumina catalysts.

The weight hourly alcohol space velocity used in the process of this invention is most suitably in the range 0.2 to 0.75 hr$^{-1}$ but substantially higher rates may be used to increase the di-methylamine/tri-methylamine ratio in the crude reaction product, provided that the correspondingly lowered conversion levels can be tolerated in the distillation section of the plant. The degree of conversion of methanol is suitably in the range 60 to 96%, or more usually in the range 75 to 95%. However, these ranges are merely indicative and the process can be operated at degrees of conversion outside these ranges.

By controlling the temperature, space velocity and degree of methanol conversion within the preferred ranges quoted hereinbefore, the man skilled in this art will be able to determine readily the process conditions which achieve the desired yield and proportions of the preferred mono- and di-methylamine products.

Nevertheless, occasions will arise when the proportions of the various products will not be optimal for the needs of the market. It is possible, for example, that more tri-methylamine than is needed will be produced. In such circumstances, it is desirable to recycle at least some of the methylamine product with or without fresh methanol and/or ammonia over a catalyst comprising an aluminosilicate zeolite, preferably over the same catalyst as is used in the process of this invention. In particular we have found that upon recycle over zeolite 5A tri-methylamine is at least partially converted to equimolar proportions of mono- and di-methylamine in the presence of excess ammonia. Recycle of MMA or DMA is also possible over this catalyst, such that some transmethylation reaction will occur to permit isolation of the three amines in a more favourable ratio to meet the demands of the market.

The N/R molar ratio, defined as the ratio of $$\frac{\text{moles of ammonia } + \text{ ammonia equivalent of recycled amine}}{\text{moles of alkyl (alcohol } + \text{ recycled amine)}}$$

fed to the reactor is of major importance. Preferably the N/R ratio is in the range 0.5 to 2.0 preferably 0.9 to 1.5. We have found that at lower levels than 0.9 by-product reactions and coke formation are liable to be troublesome and may deleteriously affect catalyst life. At N/R ratios greater than 2.0, we have found that, although tri-methylamine make is relatively low, the yield of di-methylamine is also low because both kinetics and thermodynamics act together to give high yields of mono-methylamine. We have found that it is possible to make use of the effect of varying product makes with varying N/R ratios to control the overall yield and proportions of mono-, di-, and tri-methylamines.

According to a further aspect of the present invention a process for the manufacture of methylamines comprises reacting methanol and/or dimethyl ether and ammonia in a first stage over a catalyst selective for the production of di-methylamine in preference to mono- and tri-methylamine and at a given N/R ratio, and in a second stage reacting at least some of the product from the first stage, optionally with additional fresh feed, over a selective catalyst which may be the same as or different from the catalyst in the first stage at a different N/R ratio to that used in the first stage, the catalyst in at least one of said stages comprising binderless zeolite A, preferably binderless zeolite 5A. In this aspect of the process the N/R ratio in the first stage is chosen so as to give a broadly favourable product ratio. The N/R ratio in the second stage is varied as market demands alter so that the overall product ratio matches the market demand as closely as possible.

The process of this invention is further illustrated in the following Examples.

EXAMPLES

A number of experiments were carried out in a laboratory micro-reactor by reacting a feed of methanol and ammonia over a bed of catalyst contained in the microreactor. Operating conditions and results are reported hereinafter and in Tables 1 to 8. Prior to use each catalyst was pretreated in situ with nitrogen, generally at 380° C. but occasionally at 360° C., to dry the catalyst before the methanol and ammonia were fed over it.

Catalyst Preparation Method

The catalysts used were commercial samples of binderless 5A prepared from zeolite 4A as granules or pellets or extrudates using kaolin binders and then suitably calcined and ion-exchanged. Alternatively the powdered 4A may be exchanged before aggregating although this may not lead to such high levels of exchanged ions.

The catalysts were optionally further ion-exchanged with calcium chloride or other suitable water-soluble salts solution using well-known techniques as required for laboratory testing.

EXAMPLES 1 TO 16

(Effect of Na/Ca ratio)

In Examples 1-10, the reaction temperature was 380° C., the N/R ratio 2:1 and the methanol liquid hourly space velocity was 0.31 hr$^{-1}$. A number of samples of binderless zeolite 5A catalyst were tested together with, for comparison, a calcium-exchanged binderless 4A zeolite catalyst and the untreated 4A. Results are given in Table 1 Part 1 and illustrated in FIG. 1B. Additionally, Examples 11-16 were conducted using a second micro-reactor with a further set of calcium-exchanged binderless 5A zeolite catalysts at 360° C., an N/R ratio of 1.5:1 and a methanol liquid hourly space velocity of 0.63 hr$^{-1}$. The results obtained are given in Table 1 Part 2 and plotted in FIG. 1A to show the benefits of low Na$^+$ level, particularly on selectivity towards dimethylamine production and inhibition of trimethylamine make.

TABLE 1

| Example No. | Catalyst Type | Na % wt | Ca % wt | Methanol Conversion (%) | Amine Product Split (% Molar) | | |
|---|---|---|---|---|---|---|---|
| | | | | | Mono | Di | Tri |
| 1 | Binderless 5A Sample 1 | 0.9 | 10.0 | 99 | 48 | 36 | 16 |
| 2 | Binderless 5A Sample 2 | 3.15 | 9.5 | 99.0 | 52 | 32 | 16 |
| 3 | Binderless 5A Sample 3 | 0.77 | 10.3 | 99.6 | 46 | 36 | 18 |
| 4 | Binderless 5A Sample 3 | 0.77 | 10.3 | 99.1 | 50 | 36 | 14 |

TABLE 1-continued

| Example No. | Catalyst Type | Na % wt | Ca % wt | Methanol Conversion (%) | Amine Product Split (% Molar) | | |
|---|---|---|---|---|---|---|---|
| | | | | | Mono | Di | Tri |
| 5 | Binderless 5A Sample 3 | 0.77 | 10.3 | 99.3 | 44.5 | 36 | 19.5 |
| 6 | Binderless 5A Sample 4 | 2.82 | 9.0 | 99.1 | 46 | 32.5 | 21.5 |
| 7 | Binderless 5A Sample 5 | 4.36 | 6.85 | 98.8 | 40.5 | 26.5 | 33 |
| 8 | Binderless 5A Sample 6 | 1.09 | 12.3 | 99 | 49.5 | 40.5 | 10 |
| 9 | Binderless 5A Sample 7 | 1.2 | 11.0 | 98.5 | 44 | 36 | 20 |
| 10 | Binderless 5A Sample 8 | 1.9 | 11.4 | 99 | 44.5 | 38 | 17.5 |
| Comp. A | Ca exchanged Binderless 4A | 0.5 | 10.3 | 98.5 | 48.5 | 34.5 | 17 |
| Comp. B | Binderless 4A | 9.4 | 0.2 | 34 | 54 | 24 | 22 |
| 11 | Ca exchanged Binderless 5A | 0.17 | 11.7 | 98 | 47 | 45 | 8 |
| 12 | Ca exchanged Binderless 5A | 0.11 | 10.8 | 99 | 48 | 45 | 7 |
| 13 | Ca exchanged Binderless 5A | 0.05 | 11.2 | 98.5 | 45 | 48 | 7 |
| 14 | Ca exchanged Binderless 5A | 0.06 | 11.2 | 98 | 46 | 47 | 7 |
| 15 | Binderless 5A | 1.1 | 12.3 | 97 | 47.5 | 40.5 | 12 |
| 16 | Binderless 5A | 1.9 | 11.4 | 98 | 46 | 40 | 14 |

The value of low $Na^+$ in enhancing the dimethylamine make is clear from the results in Table 1. The effect on MMA and TMA makes is less clear because of the scatter in results caused by relatively small variations in N/R ratio. DMA make is much less sensitive to N/R ratio than MMA/TMA ratio with zeolite 5A catalyst as with other methanol amination catalysts.

EXAMPLES 17 TO 19

(Zeolite A exchanged with various cations)

Binderless 4A zeolite was ion-exchanged with magnesium, cerium and lanthanum salts, using the earlier described methods, and the catalysts were tested at 340°–360° C., at an N/R ratio of 1.5 and at an alcohol hourly space velocity of 0.63 hr$^{-1}$. The results in Table 2 show that magnesium A has some ability to suppress formation of trimethylamine and that the rare-earth forms although of relatively low activity, also showed some similar selectivity.

EXAMPLES 20 TO 22

(Effect of binder)

In these experiments at 380° C. and at constant N/R ratio, a sample of binderless 5A zeolite was tested against a standard 5A zeolite (that is, zeolite 5A having the usual clay binder) and against a calcium-exchanged standard (i.e. with binder) zeolite 4A catalyst. The results are given in Table 3 Part 1, which includes, for comparison, values from an experiment using a nonselective silica-alumina catalyst and the thermodynamic equilibrium level. Some additional experiments with other clay-bound zeolite A's showed that the presence of a binder may not totally suppress selectivity to dimethylamine production, as indicated in example 19 and comparative examples F and G in Table 3 part 2. These latter three experiments were carried out at 360° C. and at an alcohol hourly space velocity of 0.63 hr$^{-1}$.

TABLE 2

| Example No. | Catalyst | Reaction temperature (°C.) | Methanol Conversion (%) | Amine Product Split (% Molar) | | |
|---|---|---|---|---|---|---|
| | | | | Mono | Di | Tri |
| 17 | Magnesium A | 360 | 99.3 | 32 | 28 | 40 |
| 18 | Magnesium A | 340 | 89.5 | 33 | 26.5 | 40 |
| 19 | Cerium A | 360 | 88 | 38 | 24 | 38 |
| 20 | Lanthanum A | 360 | 91 | 38 | 25 | 37 |
| | Thermodynamic equilibrium level at 360° C. | | — | 31.5 | 26 | 42.5 |

TABLE 3

| Example No. | Catalyst Type | Na % wt | Ca % wt | Methanol Conversion (%) | Amine Product Split (% Molar) | | |
|---|---|---|---|---|---|---|---|
| | | | | | Mono | Di | Tri |
| 20 | Binderless 5A Sample 4 | 2.82 | 9.0 | 99.1 | 46 | 32.5 | 21.5 |
| 21 | Binderless 5A Sample 1 | 0.9 | 10.0 | 99 | 48 | 36 | 16 |
| Comp. C | Standard 5A | 4.0 | 8.4 | 90.2 | 43 | 28 | 29 |
| Comp. D | Ca-exchanged standard 4A | 0.91 | 8.7 | 98 | 38 | 25.5 | 36.5 |
| Comp. E | Commercial Silica-alumina Catalyst | — | — | 92 | 38 | 25.5 | 36.5 |
| | Thermodynamic equilibrium value | — | — | 99.7 | 40 | 27 | 33 |
| 22 | Clay-bound 4A | 9.3 | <0.5 | 50 | 36 | 22 | 42 |
| Comp. F | Clay-bound 5A | 2.3 | 7.5 | 82 | 53 | 33 | 14 |
| Comp. G | Ca exchanged Clay-bound 5A | 0.5 | 9.0 | 82 | 54.5 | 33 | 12.5 |

It can be seen from the results in Table 3 Part 1 that the two standard catalysts are, within experimental error, unselective to di-methylamine when compared with the binderless 5A zeolite catalyst. However, the examples in Table 3 part 2 demonstrate that even where the binder level is low or for other reasons does not totally suppress selectivity the effect is strongly deleterious. In such circumstances it is generally necessary to operate the catalytic process at low conversions if any selectivity is to be observed, and it is further demonstrated that ion-exchange treatment of such a catalyst is not substantially beneficial.

EXAMPLES 23 TO 41

(Effect of recycle over amorphous and zeolite catalysts)

In these experiments, the recycle of products produced in the process of the invention was simulated by passing a feed of mono-, di- or trimethylamine with an excess of ammonia over a number of different types of catalyst. The results are shown in Table 4 for comparison of recycle of TMA using the catalyst of this patent and amorphous silica-alumina. In Table 5 results are shown for examples where several variations of feed composition and different batches of binderless zeolite 5A were used. These examples simultaneously illustrate the embodiment of the invention in which two reaction stages are used.

TABLE 4

| Example No. | Catalyst | Feed Composition | | | Temperature °C. | TMA Conversion % | Molar Product Composition | | | | MMA/DMA Ratio |
|---|---|---|---|---|---|---|---|---|---|---|---|
| | | % NH₃ | % TMA | N/R Molar | | | % NH₃ | % MMA | % DMA | % TMA | |
| 23 | Binderless 5A | 60.4 | 39.6 | 0.84 | 370 | 23.7 | 50.7 | 8.9 | 9.8 | 30.2 | 48:52 |
| 24 | Zeolite (crushed to 16-36 mesh pieces) | 66.6 | 33.5 | 1.01 | 380 | 22.4 | 59.1 | 7.7 | 7.2 | 26.0 | 52.48 |
| 25 | | 74.4 | 25.6 | 1.32 | 390 | 30.3 | 66.6 | 8.4 | 7.1 | 17.9 | 54:46 |
| 26 | Amorphous silica-alumina | 44.8 | 55.3 | 0.59 | 370 | 24.6 | 31.2 | 10.9 | 16.2 | 41.7 | 40:60 |
| 27 | | 46.8 | 53.2 | 0.62 | 380 | 26.5 | 32.7 | 12.1 | 16.1 | 39.1 | 43.57 |
| 28 | | 49.4 | 50.5 | 0.65 | 390 | 28.7 | 34.9 | 13.0 | 16.1 | 36.0 | 45:55 |
| 29 | | 49.3 | 50.7 | 0.65 | 400 | 29.6 | 34.3 | 13.5 | 16.5 | 35.7 | 45:55 |

TABLE 5

| Example No. | Temp. °C. | Feed (1:1 molar) | N/R | Mole % Product Composition (Normalised) | | | | Amine Split (% Molar) | | |
|---|---|---|---|---|---|---|---|---|---|---|
| | | | | NH₃ | MMA | DMA | TMA | MMA | DMA | TMA |
| 30 | 370 | TMA NH₃ | 0.68 | 45.2 | 5.0 | 6.6 | 43.2 | 9.1 | 12.0 | 78.9 |
| 31 | 380 | TMA NH₃ | 0.69 | 45.5 | 5.8 | 7.7 | 41.1 | 10.5 | 14.0 | 75.4 |
| 32 | 390 | TMA NH₃ | 0.63 | 39.7 | 6.4 | 9.1 | 44.8 | 10.7 | 15.1 | 74.2 |
| 33 | 370 | DMA NH₃ | 1.10 | 52.8 | 13.8 | 23.2 | 10.2 | 29.3 | 49.1 | 21.6 |
| 34 | 380 | DMA NH₃ | 1.04 | 50.8 | 14.8 | 21.6 | 12.8 | 30.1 | 44.0 | 26.0 |
| 35 | 390 | DMA NH₃ | 1.06 | 51.9 | 14.8 | 20.1 | 13.3 | 30.8 | 41.7 | 27.5 |
| 36 | 370 | MMA NH₃ | 2.41 | 62.9 | 33.0 | 3.7 | 0.5 | 88.7 | 9.9 | 1.3 |
| 37 | 380 | MMA NH₃ | 2.38 | 62.0 | 34.1 | 3.6 | 0.3 | 89.9 | 9.4 | 0.7 |
| 38 | 390 | MMA NH₃ | 2.28 | 61.6 | 33.3 | 4.6 | 0.5 | 86.8 | 11.9 | 1.3 |
| 39 | 370 | MMA TMA | 0.54 | 9.3 | 34.8 | 16.9 | 39.0 | 38.3 | 18.7 | 43.0 |
| 40 | 380 | MMA TMA | 0.52 | 9.8 | 29.2 | 19.3 | 41.7 | 32.4 | 21.4 | 46.2 |
| 41 | 390 | MMA TMA | 0.51 | 10.4 | 28.2 | 17.6 | 43.7 | 31.5 | 19.7 | 48.8 |

From the results in Table 4 it is clear that use of the amorphous silica-alumina catalyst gives, as expected, the thermodynamic equilibrium composition but that the use of the 5A zeolite does not give complete conversion of tri-methylamine. This may be because of incomplete absorption of tri-methylamine into the zeolite cages. However there is also some transmethylation over the zeolite catalyst presumably due to the effect of surface or unselective acidic sites. The overall result is to give a product split approximating to that which would have been achieved using pure methanol over that type of catalyst.

The results in Table 5 illustrate that transmethylation occurs when feed compositions containing other methylamines are used.

EXAMPLES 42 AND 43

(Effect of catalyst conditioning)

Experiments were carried out using two samples of binderless 5A zeolite and results were recorded at various times after start-up. The results are given in Table 6 and clearly show how the catalyst requires some time on line before it gives its best performance in terms of yield of di-methylamine.

TABLE 6

| Hrs on line | Temp °C. | Methanol HSV | N/R Ratio Molar | % Molar Split in Product | | | Conv % |
|---|---|---|---|---|---|---|---|
| | | | | Mono | Di | Tri | |
| | | First Catalyst sample (Example 42) | | | | | |
| 129 | 380 | 0.31 | 2.3 | 39.6 | 27.5 | 32.9 | 99.2 |
| 136 | 400 | 0.31 | 2.2 | 39.5 | 27.3 | 33.2 | 99.3 |
| 243 | 400 | 0.31 | 1.9 | 36.8 | 29.6 | 33.6 | 98.0 |
| 432 | 400 | 0.31 | 2.1 | 44.8 | 37.1 | 18.1 | 98.1 |
| | | Second Catalyst Sample (Example 43) | | | | | |
| 128 | 380 | 0.31 | 2.2 | 41.5 | 26.4 | 32.1 | 98.6 |
| 136 | 400 | 0.31 | 2.1 | 38.3 | 26.4 | 35.3 | 98.9 |
| 412 | 380 | 0.31 | 1.9 | 48.2 | 36.5 | 15.3 | 96.3 |
| 420 | 400 | 0.31 | 2.0 | 44.5 | 35.1 | 20.4 | 98.0 |

EXAMPLES 44 TO 75

(Effect of Pressure)

A number of runs were carried out using a binderless 5A zeolite at various reaction pressures and results are given in Table 7. These show that both methanol conversion and DMA make were not significantly affected by pressure, but MMA make increased and TMS make decreased at low pressure.

TABLE 7

| Example No. | Temp °C. | Pressure psi | Methanol HSV | N/R Ratio (molar) | % Molar Split of Products | | | % Weight Split of Products | | | Conv % |
|---|---|---|---|---|---|---|---|---|---|---|---|
| | | | | | Mono | Di | Tri | Mono | Di | Tri | |
| 44 | 360 | 250 | 0.31 | 2.0 | 60.3 | 32.8 | 6.9 | 49.8 | 39.8 | 10.9 | 84.9 |
| 45 | 360 | 150 | 0.31 | 2.1 | 56.8 | 33.7 | 9.5 | 45.9 | 39.5 | 14.6 | 87.2 |
| 46 | 360 | 100 | 0.31 | 2.0 | 62.3 | 30.4 | 7.3 | 51.8 | 36.6 | 11.6 | 84.4 |
| 47 | 360 | 80 | 0.31 | 1.95 | 62.9 | 30.1 | 7.0 | 52.5 | 36.4 | 11.1 | 83.0 |
| 48 | 360 | 250 | 0.37 | 2.05 | 57.6 | 33.4 | 9.0 | 46.7 | 39.4 | 13.9 | 89.0 |
| 49 | 360 | 150 | 0.37 | 1.4 | 54.2 | 35.9 | 9.9 | 43.3 | 41.6 | 15.0 | 79.3 |
| 50 | 360 | 80 | 0.37 | 1.6 | 60.0 | 31.8 | 8.2 | 49.3 | 37.9 | 12.8 | 78.4 |
| 51 | 360 | 250 | 0.45 | 1.0 | 53.1 | 38.7 | 8.2 | 42.5 | 45.0 | 12.5 | 66.7 |
| 52 | 360 | 150 | 0.45 | 1.0 | 48.8 | 38.5 | 12.7 | 37.9 | 43.4 | 18.7 | 72.9 |

TABLE 7-continued

| Example No. | Temp °C. | Pressure psi | Methanol HSV | N/R Ratio (molar) | % Molar Split of Products | | | % Weight Split of Products | | | Conv % |
|---|---|---|---|---|---|---|---|---|---|---|---|
| | | | | | Mono | Di | Tri | Mono | Di | Tri | |
| 53 | 360 | 80 | 0.45 | 1.7 | 54.0 | 35.0 | 11.0 | 42.9 | 40.4 | 16.7 | 75.6 |
| 54 | 360 | 250 | 0.56 | 0.55 | 43.5 | 38.9 | 17.6 | 32.7 | 42.4 | 24.9 | 54.1 |
| 55 | 380 | 250 | 0.31 | 1.85 | 46.1 | 37.2 | 16.7 | 35.0 | 41.0 | 24.0 | 95.5 |
| 56 | 380 | 150 | 0.31 | 1.95 | 48.2 | 36.5 | 15.3 | 37.0 | 40.7 | 22.3 | 96.3 |
| 57 | 380 | 100 | 0.31 | 2.5 | 55.3 | 34.2 | 10.5 | 44.3 | 39.8 | 15.9 | 98.1 |
| 58 | 380 | 80 | 0.31 | 1.9 | 55.1 | 35.4 | 9.5 | 44.3 | 41.2 | 14.5 | 94.1 |
| 59 | 380 | 150 | 0.37 | 1.3 | 41.1 | 39.9 | 19.0 | 30.4 | 42.9 | 26.7 | 90.9 |
| 60 | 380 | 80 | 0.37 | 1.5 | 51.1 | 37.1 | 11.8 | 40.1 | 43.3 | 17.6 | 90.8 |
| 61 | 380 | 250 | 0.45 | 1.3 | 44.2 | 39.6 | 16.2 | 33.4 | 43.4 | 23.2 | 90.2 |
| 62 | 380 | 150 | 0.45 | 1.0 | 39.8 | 41.7 | 18.5 | 29.4 | 44.7 | 25.9 | 84.6 |
| 63 | 380 | 80 | 0.45 | 1.1 | 44.7 | 39.8 | 15.5 | 33.9 | 43.7 | 22.4 | 87.7 |
| 64 | 380 | 250 | 0.56 | 0.55 | 36.8 | 39.0 | 24.2 | 26.6 | 40.7 | 32.7 | 68.5 |
| 65 | 400 | 250 | 0.31 | 2.05 | 43.9 | 32.1 | 24.0 | 32.3 | 34.2 | 33.5 | 98.5 |
| 66 | 400 | 190 | 0.31 | 2.0 | 44.5 | 35.1 | 20.4 | 33.2 | 37.1 | 28.9 | 98.0 |
| 67 | 400 | 100 | 0.31 | 2.6 | 49.7 | 34.1 | 16.2 | 38.2 | 38.1 | 23.7 | 99.1 |
| 68 | 400 | 80 | 0.31 | 2.0 | 49.2 | 36.9 | 13.9 | 38.1 | 41.4 | 20.5 | 98.2 |
| 69 | 400 | 250 | 0.37 | 1.55 | 43.0 | 37.7 | 19.3 | 32.1 | 40.7 | 27.2 | 97.2 |
| 70 | 400 | 150 | 0.37 | 1.55 | 38.2 | 38.3 | 23.4 | 27.7 | 40.4 | 31.9 | 95.5 |
| 71 | 400 | 80 | 0.37 | 1.5 | 44.8 | 37.9 | 17.3 | 33.8 | 41.4 | 24.8 | 96.7 |
| 72 | 400 | 250 | 0.45 | 1.0 | 37.2 | 41.7 | 21.1 | 27.0 | 44.1 | 28.9 | 87.8 |
| 73 | 400 | 150 | 0.45 | 1.05 | 34.1 | 38.6 | 27.3 | 24.1 | 39.4 | 36.5 | 91.2 |
| 74 | 400 | 80 | 0.45 | 1.1 | 36.6 | 41.2 | 22.2 | 26.4 | 43.1 | 30.5 | 95.7 |
| 75 | 400 | 250 | 0.56 | 0.55 | 28.4 | 34.8 | 36.8 | 19.1 | 34.0 | 46.9 | 78.1 |

EXAMPLES 76 TO 81

(Effect of Temperature)

A series of experiments was carried out using a binderless 5A zeolite at various, gradually increasing, temperatures. The results are given in Table 8 and show that the proportion of di-methylamine in the product falls away as the temperature is increased until, at 480° C., the amount of di-methylamine is no more than can be obtained using conventional catalysts at the more usual reaction temperatures.

TABLE 8

| Example No. | Temp °C. | Press psi | Methanol HSV | Total SV moles/l Prod | N/R Ratio | % Molar Split of Product | | | Conv % |
|---|---|---|---|---|---|---|---|---|---|
| | | | | | | Mono | Di | Tri | |
| 76 | 380 | 250 | 0.37 | 0.023 | 1.4 | 53.76 | 35.94 | 10.29 | 91.6 |
| 77 | 400 | 250 | 0.37 | 0.023 | 1.7 | 53.51 | 34.39 | 12.10 | 96.9 |
| 78 | 420 | 250 | 0.37 | 0.023 | 1.6 | 48.73 | 34.67 | 16.60 | 98.0 |
| 79 | 440 | 250 | 0.37 | 0.023 | 1.4 | 43.12 | 32.75 | 24.13 | 98.35 |
| 80 | 460 | 250 | 0.37 | 0.023 | 1.3 | 42.31 | 30.17 | 27.53 | >98.5 |
| 81 | 480 | 250 | 0.45 | 0.022 | 1.2 | 37.00 | 28.67 | 34.33 | >98.5 |

Note:
Substantial by-product make (especially methane) at 425° C.

I claim:

1. A process for the manufacture of methylamines which comprises reacting a feed comprising methanol, dimethylether or mixtures thereof and ammonia over a catalyst comprising binderless zeolite A in the alkaline earth form.

2. A process as claimed in claim 1 in which the process is operated at weight hourly alcohol space velocity in the range 0.2 to 0.75 hrs$^{-1}$ and at an N/R ratio which is defined as moles of ammonia+ammonia equivalent of recycled amine moles of alkyl (alcohol+recycled amine) is in the range of 0.5 to 2.0.

3. A process as claimed in claim 1 in which the binderless zeolite A is in the calcium form.

4. A process as claimed in claim 1 in which the catalyst has a content of alkali metal which is less than 4% by weight.

5. A process as claimed in claim 4 in which the catalyst is essentially free of alkali metal.

6. A process as claimed in claim 1 in which the catalyst comprising binderless zeolite A has been aged before use in the process.

7. A process as claimed in claim 1 in which the process is operated at a temperature within the range 325° to 400° C.

8. A process as claimed in claim 1 in which at least some of the methylamine product is recycled over a catalyst comprising an aluminosilicate zeolite.

9. A process as claimed in claim 1 which comprises reacting methanol and/or dimethyl ether and ammonia in a first stage over a catalyst selective for the production of di-methylamine in preference to mono- and tri-methylamine and at a given N/R ratio, and in a second stage reacting at least some of the product from the first stage, optionally with additional fresh feed, over a selective catalyst which may be the same as or different from the catalyst in the first stage at a different N/R ratio to that used in the first stage, the catalyst in at least one of said stages comprising binderless zeolite A.

* * * * *